US012636480B2

(12) United States Patent
Berg et al.

(10) Patent No.:  US 12,636,480 B2
(45) Date of Patent:       May 26, 2026

(54) COUPLING SYSTEM FOR A CLOSED FLUID TRANSFER SYSTEM

(71) Applicant: B. Braun Melsungen AG, Melsungen (DE)

(72) Inventors: Karl Martin Berg, Melsungen (DE); Nathanael Fischer, Bad Hersfeld (DE); Florin Kopp, Schortens (DE); Gerrit Seidel, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 1023 days.

(21) Appl. No.: 17/774,566

(22) PCT Filed: Nov. 19, 2020

(86) PCT No.: PCT/EP2020/082624
§ 371 (c)(1),
(2) Date: May 5, 2022

(87) PCT Pub. No.: WO2021/099438
PCT Pub. Date: May 27, 2021

(65) Prior Publication Data
US 2022/0387775 A1      Dec. 8, 2022

(30) Foreign Application Priority Data

Nov. 21, 2019     (DE) ..................... 10 2019 217 987.8

(51) Int. Cl.
*A61M 39/10*              (2006.01)
(52) U.S. Cl.
CPC ..... *A61M 39/10* (2013.01); *A61M 2039/1027* (2013.01)
(58) Field of Classification Search
CPC ...... A61M 2039/267; A61M 2039/268; A61M 39/1011; A61M 2039/1016; F16L 37/252
See application file for complete search history.

(56) References Cited

U.S. PATENT DOCUMENTS 5,492,147  A      2/1996   Challender et al.
6,964,406  B2    11/2005   Doyle
(Continued)

FOREIGN PATENT DOCUMENTS

JP          2018103037  A      7/2018
WO        2018009653  A1      1/2018

OTHER PUBLICATIONS

Search Report received in International Application No. PCT/EP2020/082624 dated Feb. 18, 2021, with translation, 4 pages.

*Primary Examiner* — Kami A Bosworth
(74) *Attorney, Agent, or Firm* — CM Law; Christopher A. Rothe

(57)                ABSTRACT

A coupling system for a closed fluid transfer system includes at least one coupling member and at least one counter coupling member. The coupling member includes a coupling member sealing member that has at least one reversibly openable and closable coupling member sealing member opening facing a coupling side of the coupling member. At least one activation member engages the coupling member sealing member. The counter coupling member includes a counter coupling member sealing member that includes a reversibly openable and closable counter coupling member sealing member opening facing a coupling side of the counter coupling member, and is configured to move the activation member to a position with minimum distance to a fluid connection of the coupling member upon coupling of the coupling member and the counter coupling member. The counter coupling member sealing member opening is opened in a connected state by the coupling member sealing member.

17 Claims, 4 Drawing Sheets

(56) References Cited

U.S. PATENT DOCUMENTS

| | | |
|---|---|---|
| 9,308,362 B2 | 4/2016 | Mansour et al. |
| 2005/0087715 A1 | 4/2005 | Doyle |
| 2006/0192164 A1 | 8/2006 | Korogi et al. |
| 2014/0246616 A1* | 9/2014 | Fangrow ................. F16L 29/00 251/148 |
| 2014/0276458 A1 | 9/2014 | Mansour et al. |
| 2019/0184152 A1 | 6/2019 | Kakinoki |

* cited by examiner

COUPLING SYSTEM FOR A CLOSED FLUID TRANSFER SYSTEM

CROSS-REFERENCES TO RELATED APPLICATIONS

This application is the United States national stage entry of International Application No. PCT/EP2020/082624, filed Nov. 19, 2020, and claims priority to German Application No. 10 2019 217 987.8, filed Nov. 21, 2019. The contents of International Application No. PCT/EP2020/082624 and German Application No. 10 2019 217 987.8 are incorporated by reference herein in their entireties.

FIELD

The invention relates to a coupling system for a closed fluid transfer system.

BACKGROUND

Various drugs may have an effect that is hazardous to health in the event of improper contact. For example, CMR drugs (carcinogenic-mutagen-reprotoxic drugs), as used in cancer therapy, damage specifically growth-intensive tumor cells during therapeutic application. Due to their mechanism of action, many of these drugs themselves have carcinogenic properties. In order to prevent contact of non-therapeutic persons with CMR drugs, closed fluid transfer systems, so-called "Closed System Transfer Devices" (CSTD), are increasingly used in the manufacture and administration of ready-to-use preparations. An important component of these closed fluid transfer systems are coupling systems that allow the safe transfer of substances hazardous to health, such as CMR drugs, and dry seal them after disconnection to protect the environment from contamination, for example by leakage or droplet formation on the surface of the coupling partners after disconnection.

Coupling systems of this type are generally associated with the terms "Dry Connection", "Automatic Self-Sealing Technology" or "Closed Connection" and are an essential component for the realization of closed fluid transfer systems, which are becoming increasingly important for the adjustment and administration of ready-to-use CMR drugs.

In a known coupling system, for example, the inside of the coupling is based on a Luer lock, resulting in a small flow gap with only very low flow. Other coupling systems may have higher fluid residues on the elastomer surfaces due to poorly superimposed geometries of the flow gaps in the elastomers used. In addition, the disinfectability of the coupling surfaces of common coupling systems is further aggravated, since at least one of the coupling partners has a recessed and thus poorly accessible coupling surface.

SUMMARY

In view of the disadvantages associated with the prior art, it is an object of the present invention to provide a coupling system for a closed fluid transfer system that improves the safe transfer of a fluid in a closed fluid transfer system in a connected state and minimizes and preferably prevents contamination of the environment in a disconnected state.

According to the invention, the coupling system for a closed fluid transfer system comprises a coupling member. The coupling member comprises a coupling member housing having a fluid connection and a coupling side, the coupling member housing having a longitudinal axis extending from the fluid connection towards the coupling side, a fluid conduit extending in the direction of the longitudinal axis from the fluid connection into the coupling member housing, a coupling member sealing member covering a fluid conduit opening of the fluid conduit facing the coupling side, wherein the coupling member sealing member comprises at least one reversibly openable and closable coupling member sealing member opening in the region of the covering of the fluid conduit opening facing the coupling side, and wherein at least one portion adjoining the coupling member sealing member opening and encompassing it, in particular the entire coupling member sealing member, is formed from an elastic material, and at least one activation member engaging the coupling member sealing member and being movable in the direction of the longitudinal axis in the coupling member housing between a position with maximum distance to the fluid connection and a position with minimum distance to the fluid connection, wherein the activation member is configured such that the coupling member sealing member opening of the coupling member sealing member is closed in the position of the activation member with maximum distance to the fluid connection, and that the coupling member sealing member opening is opened in the position of the activation member with minimum distance to the fluid connection.

The position of the activation member with maximum distance to the fluid connection corresponds to a position of the activation member in a disconnected state without a counter coupling member engaging the coupling member. The position of the activation member with minimum distance to the fluid connection corresponds to a position of the activation member in a connected state, in which the counter coupling member is connected to the coupling member for a safe fluid transfer. Alternatively, the position of the activation member with minimum distance to the fluid connection may also be a position with a small distance to the fluid connection as the distance in the connected state. In terms of securely opening the coupling member sealing member opening by the activation member, the position of the of the activation member with minimum distance corresponding to the position of the activation member in the connected state is, however, sufficient.

By moving the activation member between the positions mentioned above, i.e. positions with minimum and maximum distance, a relative movement between the activation member and the fluid conduit takes place. Since the activation member also engages at the coupling member sealing member, at least the portion of the coupling member sealing member is moved along relatively at the point of engagement of the activation member. Since, in turn, the coupling member sealing member covers the fluid conduit opening of the fluid conduit facing the coupling side, and comprises the at least one reversibly openable and closable coupling member sealing member opening in said region of covering, a tensile force by relative movement initiated by the activation member acts on the portion made of elastic material adjoining the coupling member sealing member opening and encompassing it. The coupling member sealing member opening is opened with increasing relative movement and thus increasing tensile force due to the deformation of the portion made of elastic material. In terms of the reversible opening and closing of the coupling member sealing member opening, the position of the activation member with minimum distance to the fluid connection is preferably limited to a position and thus to a maximum movement distance, at which the resulting tensile force neither exceeds the strength of a material of the coupling member sealing member exposed to the tensile force nor results in a plastic deformation of a material of the coupling member sealing member exposed to the tensile force. According to the above embodiments, the reversible opening and closing of the coupling member sealing member opening may thus be realized in a simple manner via the movement of the activation member relative to the fluid conduit in the direction of the longitudinal axis L1.

Since the activation member tensions the coupling member sealing member when moving towards the fluid connection, i.e. works quasi against a spring force of the coupling member sealing member, the coupling member sealing member strives to return to its initial state when the force applied by the activation member ceases. Thus, if the activation member is not intentionally moved from a position with maximum distance to the fluid connection or is retained in a position that does not correspond to the position with maximum distance to the fluid connection, it is in turn returned to this position by the coupling member sealing member, and the coupling member sealing member opening is automatically closed.

Further, the coupling system comprises a counter coupling member, comprising a counter coupling member housing having a counter coupling member fluid connection and a counter coupling side, the counter coupling member housing having a counter coupling member longitudinal axis extending from the counter coupling member fluid connection towards the counter coupling side, and a counter coupling member sealing member arranged in the counter coupling member housing and forming, together with the counter coupling member housing, at least a portion of a counter coupling side end face of the counter coupling member, wherein the counter coupling member sealing member comprises a reversibly openable and closable counter coupling member sealing member opening in the region of the counter coupling side end face, and wherein at least a portion adjoining the counter coupling member sealing member opening and encompassing it, in particular the entire counter coupling member sealing member, is formed from an elastic material.

Due to the at least partially elastic formation of the counter coupling sealing member, it is, comparable to the coupling member sealing member, reversibly openable and closable by an application of force in a simple manner. In a disconnected state, which corresponds to a state, in which no force is applied, the counter coupling member sealing member is closed. If a force is now applied in the direction towards the counter coupling member fluid connection to the end face facing the counter coupling side, i.e. the portion of the counter coupling member sealing member opening, at least the portion of the counter coupling member sealing member opening is pressed in the direction towards the counter coupling member fluid connection, and thus the counter coupling member sealing member opening is opened. When such application of force is withdrawn, the portion of the counter coupling member sealing member opening returns to an initial shape due to its elastic formation, causing the counter coupling member sealing member opening to close again.

The reversibly openable and closable counter coupling member sealing member opening is opened in a connected state by the coupling member sealing member.

For this purpose, the coupling member sealing member is less easily elastically deformable in the contact portion with the surface of the counter coupling member sealing member facing it for opening the counter coupling member sealing member opening than the corresponding contact portion of the counter coupling member sealing member. In other words, the coupling member sealing member causes the deformation of the counter coupling member sealing member to open the counter coupling member sealing member opening, and is not itself deformed by the counter coupling member sealing member. Alternatively or in addition, the opening of the counter coupling member sealing member opening takes place indirectly via the end of the fluid conduit facing the coupling side, against which the surface of the counter coupling member sealing member facing the coupling side is supported in this region.

By opening the reversibly openable and closable counter coupling member sealing member opening by the coupling member sealing member in the connected state, the respective sealing member surfaces are pressed on each other such that a dry seal and thus dry surfaces may be achieved. Thus, due to the elastic deformability, an opening of reversibly openable and closable counter coupling member sealing member opening is not opened until it is contacted by the coupling member sealing member. If, in contrast, the reversibly openable and closable counter coupling member sealing member opening would be opened, for example, in such a way that a portion of its surface facing outward in the disconnected state would be flowed around by the respective fluid during a fluid exchange, there would be a risk that patients and/or medical personnel would come into contact with these contaminated surfaces after a disconnection.

According to an embodiment, the coupling member sealing member, starting from the region of covering of the fluid conduit opening facing the coupling side, radially encompasses the fluid conduit in the direction of the fluid connection at least over a predetermined portion with respect to the longitudinal axis and comprises a projection projecting radially outwards with respect to the longitudinal axis, in particular at an end of the coupling member sealing member facing the fluid connection, on which an end of the activation member facing the fluid connection or a projection of the activation member projecting radially inwards with respect to the longitudinal axis engages.

By such configuration, not only the opening of the fluid conduit facing the coupling side is sealed by the coupling member sealing member, but also an axial portion of the fluid conduit adjoining thereto with respect to the longitudinal axis. Besides the opportunity to cover hereby also portions of the covered axial portion, the safety of the fluid-tight covering of the opening of the fluid conduit facing the coupling side is likewise increased and the tolerance requirements in comparison to an solely end face covering are decreased, respectively.

The projection of the coupling member sealing member projecting radially outwards with respect to the longitudinal axis, at which an end facing the fluid connection or a projection of the activation member projecting radially inwards with respect to the longitudinal axis engages, allows an elongation of the portion of the coupling member sealing member encompassing the fluid conduit in direction of the longitudinal axis, when the activation member is moved along the longitudinal axis towards the fluid connection. The tensile force reversibly opening the coupling member sealing member opening is applied by such elongation.

If the projection of the coupling member sealing member projecting radially outwards with respect to the longitudinal axis is provided at an end of the coupling member sealing member facing the fluid connection, the position of the activation member with minimum distance to the fluid connection, which then corresponds to a connected state, may be a position, in which the projection of the coupling member sealing member projecting radially outwards is clamp between the end of the activation member facing the fluid connection and a portion of the coupling member housing opposite to said end. Thus, the coupling member sealing member is securely retained in the connected state, whereby the opening of the coupling member sealing member opening is ensured.

The projection of the coupling member sealing member projecting radially outwards may be formed continuously in an annular shape around the fluid conduit or also only in sections.

In a further development, the fluid conduit comprises two fluid conduit portions separated from each other by a partition, each having a lateral fluid conduit portion opening, and the coupling member sealing member comprises a fluid chamber, extending radially around the fluid conduit with respect to the longitudinal axis between a coupling side coupling member sealing member portion and a fluid connection side coupling member sealing member portion, wherein the fluid connection side coupling member sealing member portion seals at least the fluid conduit portion opening of the fluid connection side fluid conduit portion in a state in which the activation member is in the position with maximum distance to the fluid connection, and the fluid chamber extends over the lateral fluid conduit portion opening of the coupling side fluid conduit portion and the lateral fluid conduit portion opening of the fluid conduit portion in a state in which the activation member is in the position with minimum distance to the fluid connection, in order to form a fluid connection between the coupling side fluid conduit portion and the fluid connection side fluid conduit portion via the fluid chamber.

In other words, the fluid conduit is portioned in two sections by the partition, wherein a fluid exchange may take place via the lateral fluid conduit portion openings, i.e. via an out surface portion of the fluid conduit. When the activation member is in a position with maximum distance to the fluid connection, the fluid connection side fluid conduit portion opening is, however, sealed by the fluid connection side coupling member sealing member portion according to the present further development such that no fluid exchange can be carried out. The opening of the coupling side fluid conduit portion facing the coupling side is sealed by the closed coupling member sealing member opening in this state. The safety against leaking of a fluid is thereby increased. Further, the coupling member sealing member comprises a fluid chamber radially encompassing the fluid conduit with respect to the longitudinal axis, which encompasses the coupling side fluid conduit portion opening. If the activation member is now moved from a position with maximum distance to the fluid connection into a position with minimum distance to the fluid connection or in a connected state, respectively, the fluid chamber is increased in the direction of the longitudinal axis. Preferably, the portion of the coupling member sealing member encompassing the fluid chamber is elastically formed such that the extension in the direction of the longitudinal axis corresponds to an elongation of the fluid chamber in said direction. By the extension of the fluid chamber, in a position of the activation member with minimum distance to the fluid connection or in a connected state, respectively, this extends at least in sections, in particular completely, over both the coupling side and fluid connection side fluid conduit portion opening, so that a fluid exchange between the coupling side and fluid connection side fluid conduit portions may take place via the fluid chamber. At the same time, in this position of the activation member, the coupling member sealing member opening is open to allow further fluid exchange with a counter coupling member described later. Thus, the opening of the fluid connection side fluid conduit portion opening and the coupling member sealing member opening may take place via the sole movement of the activation member.

In an embodiment, the projection of the coupling member sealing member projecting outwards with respect to the longitudinal axis comprises a mounting portion mounted inside the coupling member housing.

Hence, the coupling member sealing member is securely retained in the coupling member housing such that the risk of an unintended displacement and therefore a possible associated opening of the coupling member sealing member opening is reduced.

In particular, the coupling member housing comprises a coupling side housing portion and a fluid connection side housing portion along the longitudinal axis, between which the mounting portion of the coupling member sealing member is retained.

For example, the radial projection of the coupling member sealing member described previously or another portion adjoining thereto radially outwardly for such a mounting between the housing portions may be used.

In an embodiment, the activation member is formed in an annular shape, in particular wherein the ring of the activation member engages an end of the coupling member sealing member facing the fluid connection.

The annular configuration ensures that the activation member engages the coupling member sealing member in any position of insertion, even if the portions of the coupling member sealing member provided for engagement by the activation member are only provided in sections. In addition, by means of an annular configuration, at least in the region of the end of the activation member facing the coupling side, the distance provided for receiving and moving the activation member between the coupling member housing and the coupling member sealing member may be closed by the activation member in the disconnected state or in the position of the activation member with maximum distance to the fluid connection. In such event, the wall thickness of the annular portion corresponds to the distance formed between the coupling member housing and the coupling member sealing member on the coupling side.

Alternatively, the activation member may also be formed only in sections, at least in the region of its end facing the fluid connection, for example comprising only activation member portions respectively pointing in the direction of the fluid connection. In such a case, it may be ensured that the coupling member sealing member opening may only be opened in certain insertion positions of the activation member. With respect to the activation member, it should also be noted that the latter may be annular as a whole, but does not necessarily have to fully enclose the fluid channel. Likewise, it is possible to provide the activation member only over a limited section tangential with respect to the longitudinal axis or several activation members distributed along the circumference of the fluid conduit or the coupling member sealing member, respectively.

In a further development, the coupling member housing comprises at least one retaining structure on the coupling side, in particular a retaining structure projecting on the coupling side axially beyond the coupling member sealing member with respect to the longitudinal axis, by which a counter coupling member can be retained in a connected state.

Since at least a portion of the coupling member dealing member is elastically formed and the activation member when being moved from the position with maximum distance to the fluid connection, in which at least the elastic portion is not biased with respect to the moving direction of the activation member, works against a spring force of the coupling member sealing member, the retaining structure allows maintaining the connected state without the need to continue to apply an active retaining force, for example by a user.

In particular, the retaining structure is formed by at least two retention arms having snap-fits or of being annular shape.

If retaining arms are provided only in sections, accessibility to surfaces requiring disinfection, such as the coupling side end face of the coupling member sealing member, is improved. The at least two retaining arms are arranged in such a way that tilting of a counter coupling member to be retained via them is avoided as far as possible. For example, two retaining arms are arranged substantially opposite each other or three retaining arms are arranged at a distance of substantially 120° from each other. An annular configuration of the retaining structure may alternatively enable further sealing between the coupling member and a counter coupling member corresponding thereto.

The use of snap-fits to engage a counter coupling member allows the counter coupling member to be secured in a predetermined position. Alternatively, the retaining structure may comprise threaded portions to bridge a tolerance range or otherwise allow positional adjustments to be made.

In an embodiments, a counter coupling side end of the counter coupling member housing is engageable with the at least one activation member of the coupling member, and is movable together therewith into the coupling member housing towards the fluid connection of the coupling member.

For this purpose, the counter coupling side end of the counter coupling member housing is formed in particular annularly, but may also be formed only in sections. In addition, the counter coupling member end of the counter coupling member housing has a radial thickness with respect to the counter coupling member longitudinal axis that is configured to be movable into the coupling member housing between the coupling member housing and the coupling member sealing member. In particular, the radial thickness corresponds substantially to the radial thickness of the activation member.

In particular, the counter coupling side end of the counter coupling member housing is formed as an axial projection with respect to the counter coupling member longitudinal axis, and forms a shoulder portion together a housing portion of the counter coupling member housing adjoining thereto.

Via the shoulder portion, a stop may be formed in cooperation with the coupling member housing, the reaching of which corresponds to a connected state. By moving the counter coupling side end of the counter coupling member housing until the stop is reached in the direction of the fluid connection into the coupling member housing, the activation member is thus moved into the connected state, in particular into the position with minimum distance to the fluid connection.

In an embodiment, the counter coupling member housing comprises, on an outer surface extending axially with respect to the counter coupling member longitudinal axis, a counter coupling member retaining structure, by which the counter coupling member can be retained in a connected state with the coupling member.

As already described with regard to the coupling member in relation to the activation member, the counter coupling member may be retained in the connected state comparably without applying a further active retaining force. Without a further active retaining force or the corresponding retaining structure or counter coupling member retaining structure, respectively, the counter coupling member and the coupling member would otherwise be pressed apart via the recovery striving of the elastically formed portion of the coupling member sealing member and the counter coupling member sealing member.

In a further embodiment, the counter coupling member housing comprises a counter coupling member fluid conduit having at least one lateral counter coupling member fluid conduit opening extending in the direction of the counter coupling member longitudinal axis from the counter coupling member fluid connection towards the counter coupling side in the counter coupling member housing, and wherein the counter coupling member sealing member seals the lateral counter coupling member fluid conduit opening in a disconnected state, wherein the counter coupling member sealing member comprises, between the seal and the counter coupling member sealing member opening, a counter coupling member sealing member fluid chamber movable in the direction of the counter coupling member longitudinal axis relative to the counter coupling member fluid conduit to form a fluid connection to the interior of the counter coupling member fluid conduit via the lateral counter coupling member fluid conduit opening in the connected state.

Since the counter coupling member sealing member opening could be unintentionally opened by slight depression, unintentional leakage of any fluid in the fluid conduit from the counter coupling member fluid conduit is prevented via sealing of the counter coupling member fluid conduit opening via the counter coupling member sealing member. To provide fluid connection between the counter coupling member fluid conduit and the counter coupling member sealing member fluid chamber, the counter coupling member sealing member fluid chamber may be moved towards the counter coupling member fluid connection along the counter coupling member longitudinal axis relative to the counter coupling member fluid conduit. This may be done by displacing the counter coupling member sealing member towards the counter coupling member fluid connection or compressing at least a portion of the counter coupling member sealing member adjoining the counter coupling member sealing member fluid chamber towards the counter coupling member fluid connection, which is in particular appropriately formed of elastic material. If a displacement is provided, the counter coupling member sealing member is supported at an end of the counter coupling member sealing member facing the counter coupling member fluid connection on a spring member that is compressed against its spring force upon displacement in order to move the counter coupling member sealing member back to its initial position in terms of a disconnected state upon relief. Insofar as the counter coupling member sealing member itself or at least a portion of the counter coupling member sealing member is compressed, the counter coupling member sealing member is supported in particular at an end of the counter coupling member sealing member facing the counter coupling member fluid connection on a counter coupling member housing portion facing this end in order to be merely compressed and not displaced, so that the counter coupling member sealing member returns to its initial state when decompressed. The two variants may also be combined with each other, for example, to realize larger movement distances of the fluid chamber.

The invention further comprises a coupling system for a closed fluid transfer system, comprising at least a coupling member according to the invention and a counter coupling member according to the invention, wherein the counter coupling member is configured to move the activation member during a coupling into the position with minimum distance to the fluid connection, wherein an opening of the coupling member sealing member opening caused by the movement of the activation member does not take place until the coupling member sealing member opening is sealed to the outside by the counter coupling member.

A respective sealing is particularly achieved, when the surfaces of the coupling member sealing member and the counter coupling member sealing member facing each other are pressed against each other by a predetermined compression force. Thus, it is avoided that the fluid residues occur on the surfaces of the coupling member sealing member and/or the counter coupling member sealing member upon uncoupling of the coupling member and counter coupling member.

BRIEF DESCRIPTION OF THE DRAWING FIGURES

Features, functionalities and advantages of the invention are also described below with reference to the drawings by way of exemplary embodiments.

Figure 1:
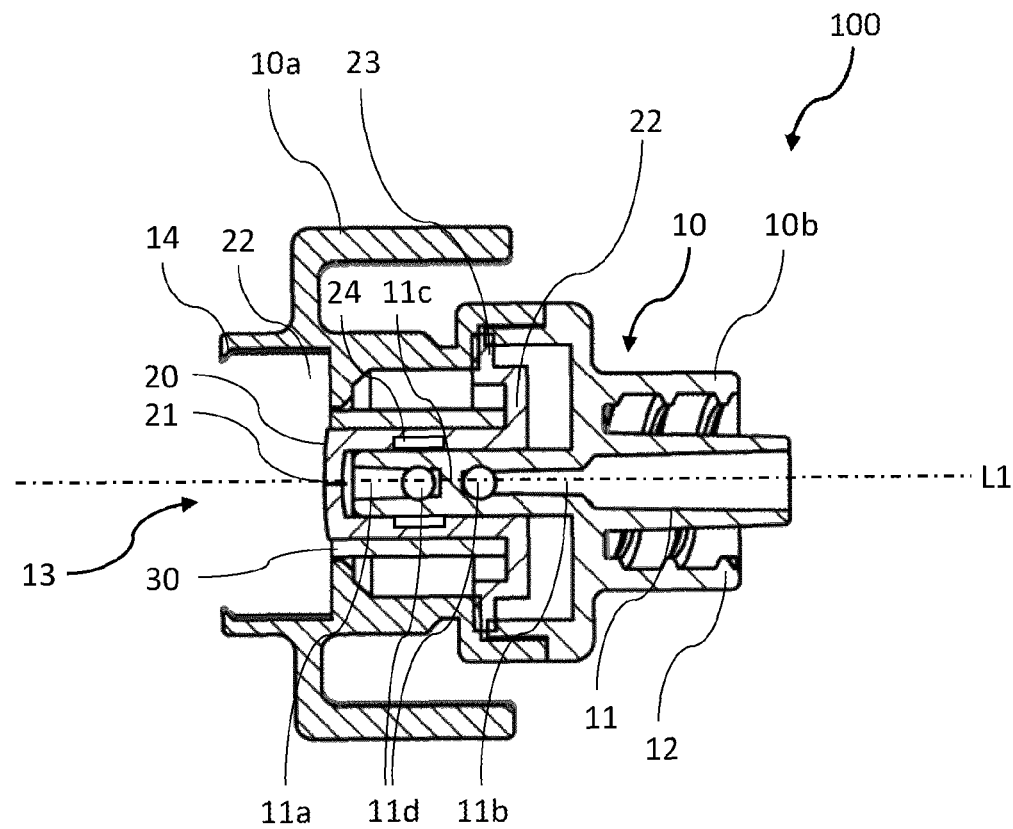
FIG. 1 shows a schematic cross-sectional view of a coupling member for use in a coupling system in a plane parallel to the longitudinal axis of the coupling member according to a first exemplary embodiment of the coupling member in a disconnected state.
Figure 2:
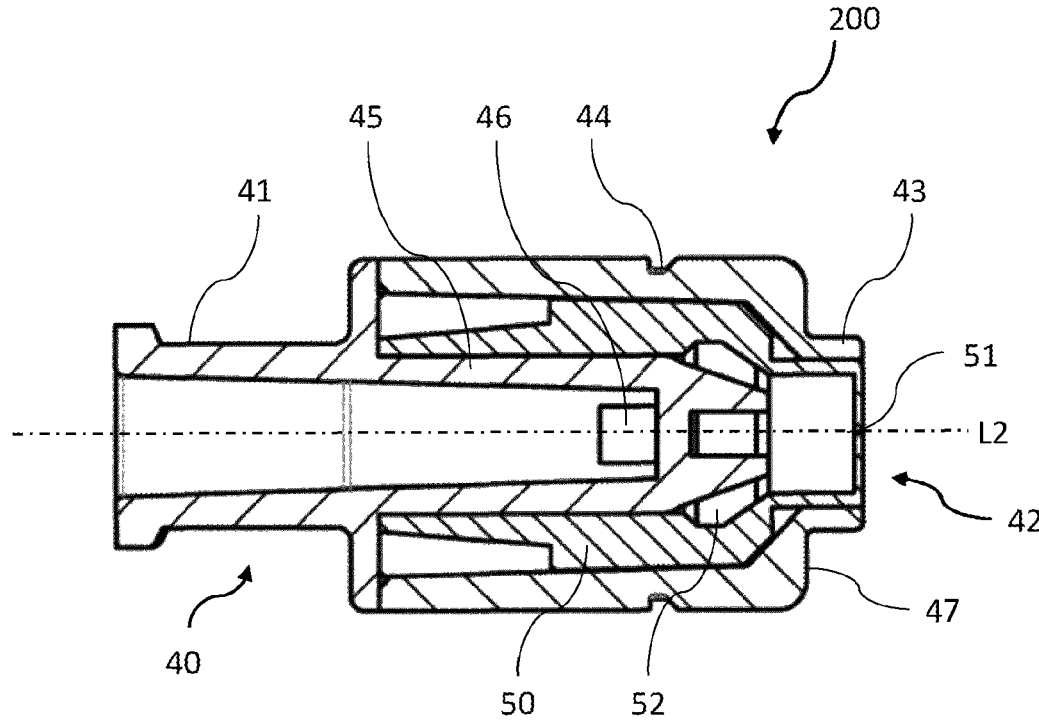
FIG. 2 shows a schematic cross-sectional view of a counter coupling member for use in a coupling system in a plane parallel to the counter coupling member longitudinal axis of the counter coupling member according to a first exemplary embodiment of the counter coupling member in a disconnected state.
Figure 3:
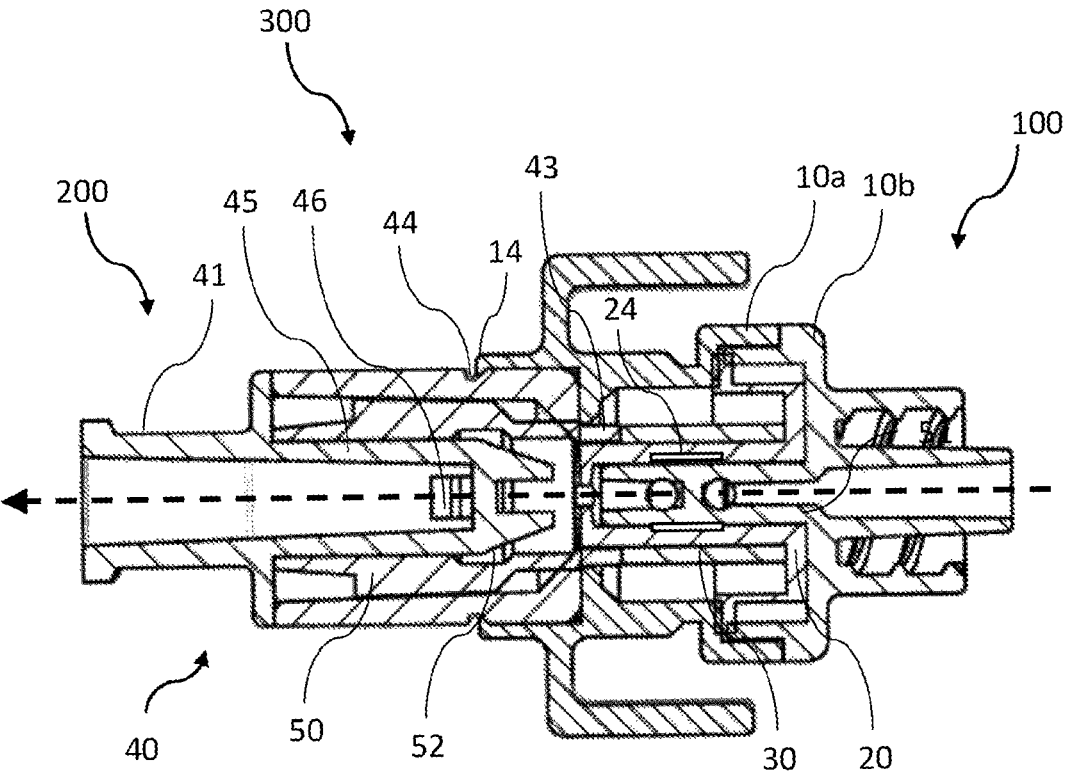
FIG. 3 shows a schematic cross-sectional view of a coupling system in a plane parallel to the longitudinal axis or counter coupling member longitudinal axis, respectively, according to the first exemplary embodiment of the coupling member and the counter coupling member in a connected state.
Figure 4:
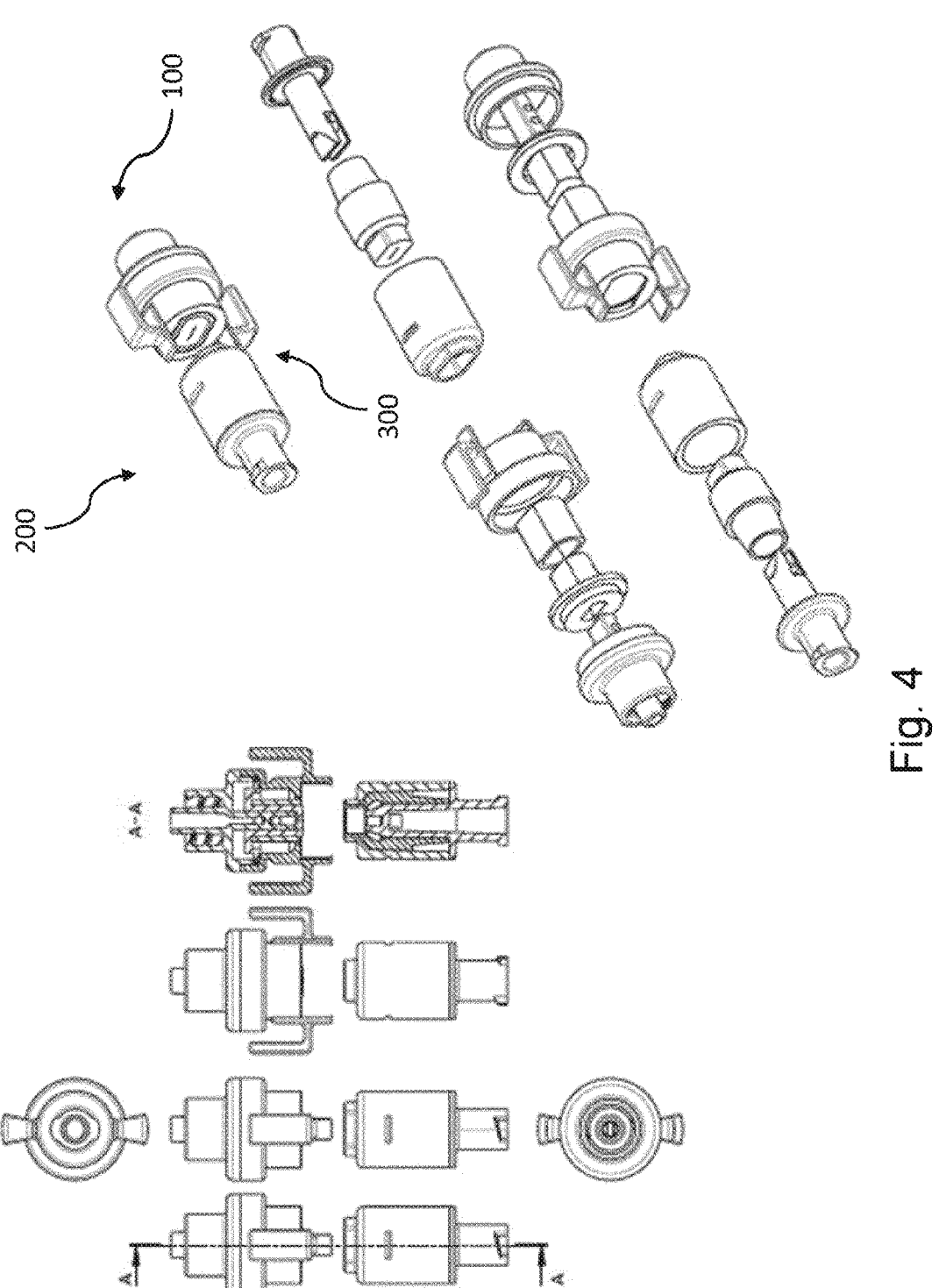
Figure 5:
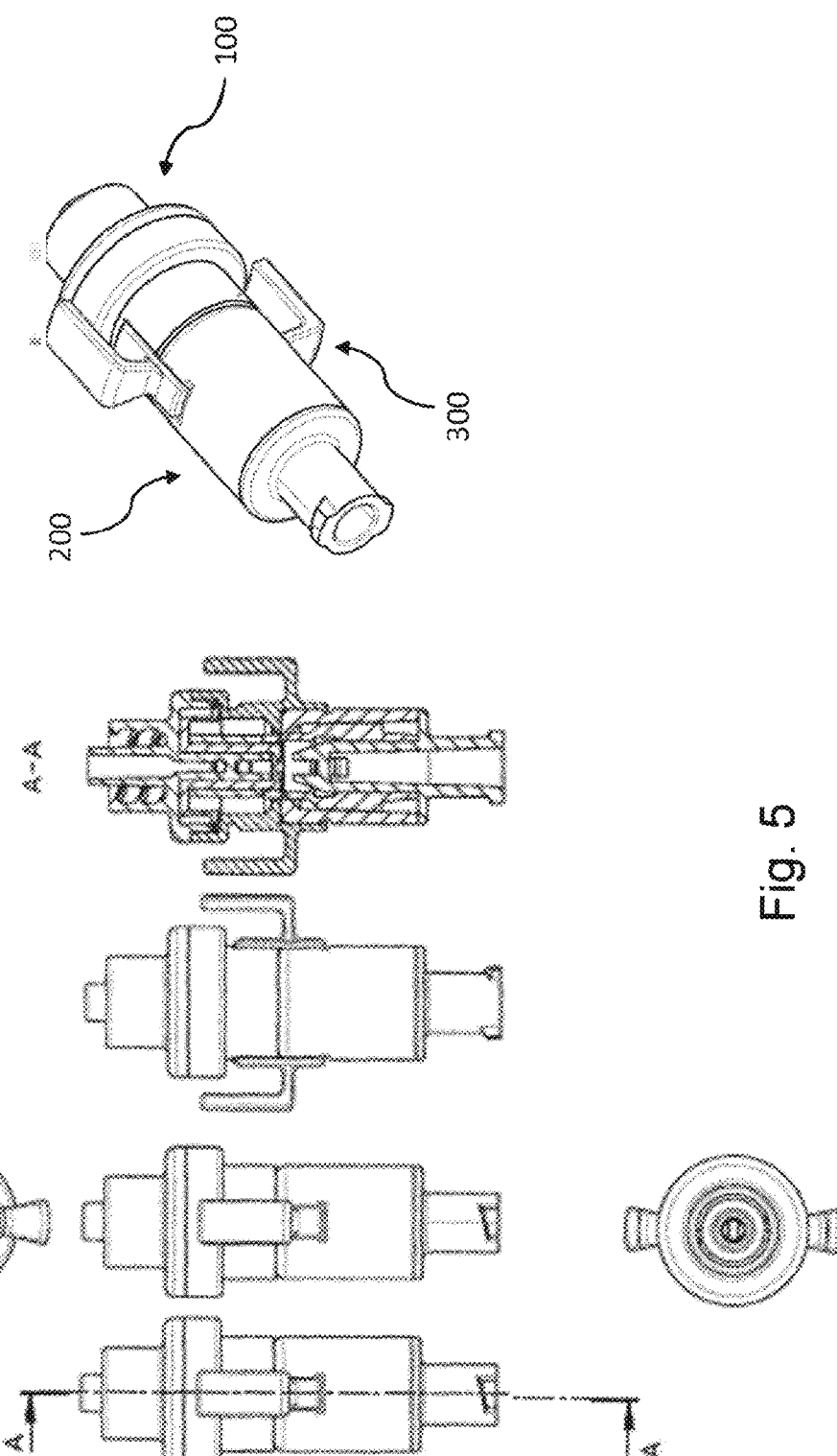

FIG. 4 shows an overview of all external views of the coupling system according to FIGS. 1 to 3 as well as a cross section along the intersection A-A, a perspective view and an exploded view in the disconnected state; and FIG. 5 shows an overview of all external views of the coupling system according to FIGS. 1 to 3 as well as a cross section along the intersection A-A and a perspective view in the connected state.

DETAILED DESCRIPTION

FIG. 1 shows a schematic cross-sectional view of a coupling member 100 for use in a coupling system 300 in a plane parallel to the longitudinal axis L1 of the coupling member 100, which extends from a fluid connection 12 towards a coupling side 13 of the coupling member housing 10. In addition to the coupling member housing 10, the coupling member 100 comprises a coupling member sealing member 20 having a reversibly openable and closable coupling member sealing member opening 21. The coupling member sealing member 20 encompasses an end of the fluid conduit 11, which is formed by the coupling member housing 10, facing the coupling side 13. The coupling member sealing member opening 21 is thereby arranged in a region of the opening of the fluid conduit 11 facing the coupling side 13. Further, the fluid conduit 11 is partitioned into a coupling side fluid conduit portion 11a and a fluid connection side fluid conduit portion 11b by a partition 11c. The coupling side fluid conduit portion 11a and the fluid connection side fluid conduit portion 11b each providing a lateral fluid conduit portion opening 11d, via which they are able to be in fluid connection.

In the embodiment shown, the coupling member sealing member 20 extends from the coupling side 13 in the direction of the longitudinal axis L1 over both fluid conduit portion openings 11d. In a position of the activation member 30 described further below, in which the coupling member sealing member 20 or parts thereof, respectively, have not been moved, that is, no tensile force has been applied, a fluid connection side coupling member sealing member portion of the coupling member sealing member 20 seals the fluid conduit portion opening 11d of the fluid connection side fluid conduit section 11b. In addition, the coupling member sealing member 20 comprises a fluid chamber 24 extending radially around the fluid conduit 11 with respect to the longitudinal axis L1 between the fluid connection side coupling member sealing member portion and a coupling side coupling member sealing member portion of the coupling member sealing member 20, that is, surrounding the fluid conduit 11 in a tangential direction. The coupling side fluid conduit portion opening 11d of the coupling side fluid conduit portion 11a is arranged in the region of the fluid chamber 24.

In order to retain the coupling member sealing member 20 in the coupling member housing 10, the coupling member sealing member 20 comprises a mounting portion 23 extending radially outwardly with respect to the longitudinal axis L1, the outer end of which is mounted in the coupling member housing 10. For this purpose, the coupling member housing 10 is formed, for example, as in this embodiment, from a coupling side housing portion 10a and a fluid connection side housing portion 10b, which clamp the mounting portion 23 between two opposing portions, for example, by screwing to each other.

For a reversible opening of the coupling member sealing member opening 21, the coupling member 100 comprises an activation member 30. The activation member 30 is formed in an annular shape and is arranged, viewed in the radial direction with respect to the longitudinal axis L1, between the coupling member sealing member 20 encompassing the fluid conduit 11 and an outer coupling member housing wall. In a position of the activation member 30 with maximum distance to the fluid connection, here a disconnected state, the end of the activation member 30 facing the coupling side 13 together with the surface of the coupling member sealing member 20 facing the coupling side 13 forms a coupling side end face. The wall thickness of the activation member substantially corresponds to the distance between the radially outer surface of the coupling member sealing member 20 and the outer coupling member housing wall for receiving the activation element 30. The term "substantially" refers in particular to the fact that the inner diameter of the activation member 30 may be slightly smaller than the radial outer diameter of the coupling member sealing member 20 prior to attachment of the activation member 30. This results in a contact pressure when attaching the activation member, which retains the activation member 30 on the coupling member sealing member 20. In the illustrated embodiment, the activation member 30 extends in the disconnected state from the coupling-side end face in the direction of the fluid connection 12 to a maximum distance therefrom that allows sufficient movement in the direction of the fluid connection 12, wherein the activation member 30 also covers the fluid portion opening 11d of the fluid connection side fluid conduit portion 11b. Due to the aforementioned covering, sealing is assisted via the fluid connection side coupling member sealing member portion, especially when the aforementioned contact pressure is provided. Furthermore, the end of the activation member 30 facing the fluid connection 12 engages a projection 22 of the coupling member sealing member 20 projecting radially outward with respect to the longitudinal axis L1.

Next, a counter coupling member according to the invention for use in a coupling system is illustrated with reference to FIG. 2 by means of a schematic cross-sectional view of a counter coupling member 200 in a plane parallel to the counter coupling member longitudinal axis L2 of the counter coupling member 200 extending from a counter coupling member fluid connection 41 of the counter coupling member housing 40 towards a counter coupling side 42. In addition to the counter coupling member housing 40, the counter coupling member 200 comprises a counter coupling member sealing member 50 disposed in the counter coupling member housing 40 and forming, together with the counter coupling member housing 40, at least a portion of a counter coupling side end face of the counter coupling member 200.

The counter coupling member housing 40 has a counter coupling side end 43 that radially adjoins and surrounds the counter coupling member sealing member 50 with respect to the counter coupling member longitudinal axis L2. This counter coupling member side end 43 forms an axial projection with respect to the counter coupling member longitudinal axis L2, and also forms with an adjoining housing portion of the counter coupling member housing 40 a shoulder portion 47, which acts as a stop for a corresponding coupling member portion of the coupling member housing 10. Furthermore, in the housing portion of the counter coupling member housing 40 adjoining the axial projection formed by the counter coupling side end 43, the counter coupling member housing 40 comprises a counter coupling member retaining structure 44, which, in the present embodiment, is formed by a circumferential groove into which the snap-fits of the retaining structure 14 of the coupling member shown in FIG. 1 can engage. A counter coupling member fluid conduit 45 extends from the counter coupling member fluid connection 41 into the counter coupling member housing 40. The counter coupling member side fluid conduit end is axially spaced from the counter coupling member side 42 with respect to the counter coupling member longitudinal axis L2 and is closed, wherein a lateral counter coupling member fluid conduit opening 46 is provided, which is sealed by the counter coupling member sealing member 50 in the disconnected state.

The counter coupling member sealing member 50 shown in FIG. 2 comprises a reversibly openable and closable counter coupling member sealing member opening 51 in the surface facing the counter coupling side 42, which is closed in a disconnected state. The counter coupling member sealing member 50 is elastically formed as such and is supported at its fluid connection side end against a housing portion of the counter coupling member housing 40 facing thereto, wherein it encompasses the counter coupling member fluid conduit 45. In the disconnected state, the counter coupling member sealing member 50 forms a counter coupling member sealing member fluid chamber 52 between the surface of the counter coupling member sealing member 50 facing the counter coupling side 42 and the closed end of the counter coupling element fluid conduit 45 facing the counter coupling side 42.

FIG. 3 shows a schematic cross-sectional view of a coupling system 300 in a plane parallel to the longitudinal axis L1 or counter coupling member longitudinal axis L2, respectively, comprising the exemplary embodiments of the coupling member 100 according to FIG. 1 and the counter coupling member 200 according to FIG. 2 and shown in the connected state.

The connected state is achieved by moving the counter coupling member 200 in the direction of the longitudinal axis L1 or counter coupling member longitudinal axis L2, respectively, towards the fluid connection 12 and/or moving the coupling member 100 in the direction of the longitudinal axis L1 or counter coupling member longitudinal axis L2, respectively, towards the counter coupling member fluid connection 41. The axial projection formed by the counter coupling member side end 43 is hereby moved into the distance between the coupling member sealing member 20 and the coupling member housing 40, thereby pushing the activation member 30 towards the fluid connection 12 from a position with maximum distance to the fluid connection 12. This stretches the coupling member sealing member 20 made of elastic material, thereby exerting a tensile force on the portion surrounding the coupling member sealing member opening 21, which opens the coupling member sealing member opening 21. As a result of the elongation of the coupling member sealing member 20, the fluid chamber 41 simultaneously expands in the axial direction with respect to the longitudinal axis L1 towards the fluid connection 12, so that the fluid conduit portion opening 11d of the fluid connection side fluid conduit portion 11b is no longer sealed. Thus, in the connected state, in which the shoulder portion 47 rests on the coupling member housing 10 and the retaining structure 14 of the coupling member 100 engages with the counter coupling member retaining structure 44, a fluid can be exchanged via the fluid connection side fluid conduit portion 11b, the fluid conduit portion opening 11d of the fluid connection side fluid conduit portion 11b, the fluid chamber 24, the fluid conduit portion opening 11d of the coupling side fluid conduit portion 11a, the coupling side fluid conduit portion 11a, and the coupling member sealing member opening 21 with the counter coupling member 200, as indicated by the arrow line in FIG. 3.

For the fluid exchange of the counter coupling element 200 with the coupling member 100, the surface facing the counter coupling side facing 42 with the counter coupling member sealing member opening 51 is pressed towards the counter coupling member fluid conduit 41 via the coupling the surface of the coupling member sealing member 20 facing the coupling side 13 or indirectly via the end of the fluid conduit 11 facing the coupling side 13, respectively. By this, the counter coupling member sealing member opening 51 is opened. At the same time, the counter coupling member sealing member 50 is compressed in the direction of the counter coupling member fluid connection 41, thereby moving the counter coupling member sealing member fluid chamber 52 towards the counter coupling member fluid connection 41 to cover at least a portion of the counter coupling member fluid conduit opening 46 in the connected state so as to allow fluid exchange. Thus, according to the arrow line, fluid exchange in the connected state may further take place via the counter coupling member sealing member opening 51 the counter coupling member fluid chamber 52, the counter coupling member fluid conduit opening 46, and the counter coupling member fluid conduit 41.

FIGS. 4 and 5 again show the above-described embodiment for the coupling system 300 in an overview of all views in the disconnected state according to FIG. 4 and in the connected state according to FIG. 5. Further configuration features of the described embodiment result from this.

The invention is not limited to the described embodiments. For example, the surface of the coupling member sealing member facing the coupling side shown in the figures is convex and the surface of the counter coupling member facing the counter coupling side is concave correspondingly. Even though this supports the respective opening formation, straight surfaces or other contouring may alternatively be provided. As already indicated, the coupling member sealing member and the counter coupling member sealing member also do not have to be formed entirely from elastic material, as in the embodiments described, but may provide this only in sections. In particular, elastic structures, such as spring joints or the like, may also be used as an alternative or supplement to the use of an elastic material.

The invention claimed is:

1. A coupling system for a closed fluid transfer system, the coupling system comprising:

a coupling member; and a counter coupling member, wherein the coupling member comprises:

a coupling member housing having a fluid connection and a coupling side, the coupling member housing having a longitudinal axis extending from the fluid connection towards the coupling side;

a fluid conduit extending in a direction of the longitudinal axis from the fluid connection into the coupling member housing; and a coupling member sealing member covering a fluid conduit opening of the fluid conduit facing the coupling side, the coupling member sealing member comprising a coupling member sealing member opening in a region where the coupling member sealing member covers the fluid conduit opening facing the coupling side, wherein the coupling member sealing member opening is reversibly openable and closable, and at least a portion of the coupling member sealing member encompassing the coupling member sealing member opening is formed from a respective elastic material, and an activation member engaging the coupling member sealing member and being movable in the direction of the longitudinal axis in the coupling member housing between a position with maximum distance to the fluid connection and a position with minimum distance to the fluid connection, wherein the activation member is configured such that the coupling member sealing member opening of the coupling member sealing member is closed in the position of the activation member with maximum distance to the fluid connection, and that the coupling member sealing member opening is opened in the position of the activation member with minimum distance to the fluid connection; and wherein the counter coupling member is for coupling with the coupling member and comprises:

a counter coupling member housing having a counter coupling member fluid connection and a counter coupling side, the counter coupling member housing having a counter coupling member longitudinal axis extending from the counter coupling member fluid connection towards the counter coupling side, and a counter coupling member sealing member arranged in the counter coupling member housing and forming, together with the counter coupling member housing, at least a portion of a counter coupling side end face of the counter coupling member, wherein the counter coupling member sealing member comprises a counter coupling member sealing member opening in a region of the counter coupling side end face, wherein the counter coupling member sealing member opening is reversibly openable and closable and wherein at least a portion of the counter coupling member sealing member encompassing the counter coupling member sealing member opening is formed from a respective elastic material, and wherein the counter coupling member is configured to cause a movement of the activation member to the position with minimum distance to the fluid connection upon coupling of the coupling member to the counter coupling member, wherein opening of the coupling member sealing member opening caused by the movement of the activation member to the position with minimum distance to the fluid connection does not occur until the coupling member sealing member opening is sealed to an external environment via the counter coupling member, wherein the counter coupling member sealing member opening is opened in a connected state by the coupling member sealing member, and wherein:

the fluid conduit comprises:

a fluid connection side fluid conduit portion having a first lateral fluid opening, a coupling side fluid conduit portion having a second lateral fluid opening, and a partition separating the fluid connection side fluid conduit portion from the coupling side fluid conduit portion, and the coupling member sealing member comprises a fluid chamber extending radially around the fluid conduit with respect to the longitudinal axis between a coupling side coupling member sealing member portion and a fluid connection side coupling member sealing member portion, wherein the fluid connection side coupling member sealing member portion seals at least the first lateral fluid opening in a state in which the activation member is in the position with maximum distance to the fluid connection, and the fluid chamber extends over the first lateral fluid opening and the second lateral fluid opening in a state in which the activation member is in the position with minimum distance to the fluid connection, in order to form a fluid connection between the coupling side fluid conduit portion and the fluid connection side fluid conduit portion via the fluid chamber.

2. The coupling system according to claim 1, wherein the coupling member sealing member, starting from the region where the coupling member sealing member covers the fluid conduit opening facing the coupling side, radially encompasses the fluid conduit in a direction of the fluid connection at least over a predetermined portion of the fluid conduit with respect to the longitudinal axis and comprises a first projection projecting radially outwards with respect to the longitudinal axis, and wherein an end of the activation member facing the fluid connection or a second projection of the activation member projecting radially inwards with respect to the longitudinal axis engages on the first projection.

3. The coupling system according to claim 2, wherein the first projection comprises a mounting portion mounted inside the coupling member housing.

4. The coupling system according to claim 3, wherein the coupling member housing comprises a coupling side housing portion and a fluid connection side housing portion along the longitudinal axis, between which the mounting portion of the coupling member sealing member is retained.

5. The coupling system according to claim 1, wherein the activation member is formed in an annular shape.

6. The coupling system according to claim 1, wherein the coupling member housing comprises a retaining structure on the coupling side by which the counter coupling member is retainable in a connected state.

7. The coupling system according to claim 6, wherein the retaining structure comprises a flexible retaining structure configured to hold the coupling member and the counter coupling member in the connected state.

8. The coupling system according to claim 7, wherein the flexible retaining structure comprises flexible retention arms with respective protrusions provided on the coupling member housing, and wherein the counter coupling member comprises recesses configured to receive the respective protrusions provided on the counter coupling member housing.

9. The coupling system according to claim 6, wherein the retaining structure is formed by at least two retention arms having snap-fits or being of annular shape.

10. The coupling system according to claim 1, wherein a counter coupling side end of the counter coupling member housing is engageable with the activation member of the coupling member, and is movable together therewith into the coupling member housing towards the fluid connection of the coupling member.

11. The coupling system according to claim 10, wherein the counter coupling side end of the counter coupling member housing is formed as an axial projection with respect to the counter coupling member longitudinal axis, and forms a shoulder portion together with a housing portion of the counter coupling member housing adjoining thereto.

12. The coupling system according to claim 1, wherein the counter coupling member housing comprises, on an outer surface extending axially with respect to the counter coupling member longitudinal axis, a counter coupling member retaining structure, by which the counter coupling member is retainable in a connected state with the coupling member.

13. The coupling system according to claim 1, wherein the counter coupling member housing comprises a counter coupling member fluid conduit having a lateral counter coupling member fluid conduit opening, extending in a direction of the counter coupling member longitudinal axis from the counter coupling member fluid connection towards the counter coupling side in the counter coupling member housing, and wherein the counter coupling member sealing member forms a seal over the lateral counter coupling member fluid conduit opening in a disconnected state, wherein the counter coupling member sealing member comprises, between the seal and the counter coupling member sealing member opening, a counter coupling member sealing member fluid chamber movable in the direction of the counter coupling member longitudinal axis relative to the counter coupling member fluid conduit to form a fluid connection to an interior of the counter coupling member fluid conduit via the lateral counter coupling member fluid conduit opening in the connected state.

14. The coupling system according to claim 1, wherein the coupling member sealing member comprises a projection extending radially outwards with respect to the longitudinal axis, and the projection comprises a mounting portion that is fixed to the coupling member housing.

15. The coupling system according to claim 14, wherein the activation member is configured to generate a force against the projection upon movement of the activation member to the position with minimum distance to the fluid connection.

16. The coupling system according to claim 1, wherein the portion of the coupling member sealing member encompassing the coupling member sealing member opening is configured to directly contact the portion of the counter coupling member sealing member encompassing the counter coupling member sealing member opening to open the counter coupling member sealing member opening in the connected state.

17. A coupling system for a closed fluid transfer system, the coupling system comprising:
   a coupling member; and
   a counter coupling member,
   wherein the coupling member comprises:
   a coupling member housing having a fluid connection and a coupling side, the coupling member housing having a longitudinal axis extending from the fluid connection towards the coupling side;
   a fluid conduit extending in a direction of the longitudinal axis from the fluid connection into the coupling member housing; and
   a coupling member sealing member covering a fluid conduit opening of the fluid conduit facing the coupling side,
   the coupling member sealing member comprising a coupling member sealing member opening in a region where the coupling member sealing member covers the fluid conduit opening facing the coupling side, wherein the coupling member sealing member opening is reversibly openable and closable, and at least a portion of the coupling member sealing member encompassing the coupling member sealing member opening is formed from a respective elastic material, and
   an activation member engaging the coupling member sealing member and being movable in the direction of the longitudinal axis in the coupling member housing between a position with maximum distance to the fluid connection and a position with minimum distance to the fluid connection,
   wherein the activation member is configured such that the coupling member sealing member opening of the coupling member sealing member is closed in the position of the activation member with maximum distance to the fluid connection, and that the coupling member sealing member opening is opened in the position of the activation member with minimum distance to the fluid connection; and
   wherein the counter coupling member is for coupling with the coupling member and comprises:
   a counter coupling member housing having a counter coupling member fluid connection and a counter coupling side, the counter coupling member housing having a counter coupling member longitudinal axis extending from the counter coupling member fluid connection towards the counter coupling side, and a counter coupling member sealing member arranged in the counter coupling member housing and forming, together with the counter coupling member housing, at least a portion of a counter coupling side end face of the counter coupling member, wherein the counter coupling member sealing member comprises a counter coupling member sealing member opening in a region of the counter coupling side end face, wherein the counter coupling member sealing member opening is reversibly openable and closable and wherein at least a portion of the counter coupling member sealing member encompassing the counter coupling member sealing member opening is formed from a respective elastic material, and wherein the counter coupling member is configured to cause a movement of the activation member to the position with minimum distance to the fluid connection upon coupling of the coupling member to the counter coupling member, wherein opening of the coupling member sealing member opening caused by the movement of the activation member to the position with minimum distance to the fluid connection does not occur until the coupling member sealing member opening is sealed to an external environment via the counter coupling member, wherein the counter coupling member sealing member opening is opened in a connected state by the coupling member sealing member, and wherein the counter coupling member housing comprises a counter coupling member fluid conduit having a lateral counter coupling member fluid conduit opening, extending in a direction of the counter coupling member longitudinal axis from the counter coupling member fluid connection towards the counter coupling side in the counter coupling member housing, and wherein the counter coupling member sealing member forms a seal over the lateral counter coupling member fluid conduit opening in a disconnected state, wherein the counter coupling member sealing member comprises, between the seal and the counter coupling member sealing member opening, a counter coupling member sealing member fluid chamber movable in the direction of the counter coupling member longitudinal axis relative to the counter coupling member fluid conduit to form a fluid connection to an interior of the counter coupling member fluid conduit via the lateral counter coupling member fluid conduit opening in the connected state.

* * * * *